United States Patent [19]

Tarjan

[11] Patent Number: 4,538,624

[45] Date of Patent: Sep. 3, 1985

[54] METHOD FOR LEAD INTRODUCTION AND FIXATION

[75] Inventor: Peter P. Tarjan, Miami, Fla.

[73] Assignee: Cordis Corporation, Miami, Fla.

[21] Appl. No.: 448,006

[22] Filed: Dec. 8, 1982

[51] Int. Cl.³ ............................................. A61N 1/04
[52] U.S. Cl. .................................. 128/784; 128/419 R
[58] Field of Search ............................... 128/783–786, 128/639, 642, 644, 303.18–303.19, 419 R, 419 P, 419 PG, 419 S, 419 C, 419 F, 421; 604/51–53, 49, 158

[56] References Cited

U.S. PATENT DOCUMENTS

| | | | |
|---|---|---|---|
| 2,154,968 | 4/1939 | Alkio | 604/49 |
| 3,474,791 | 10/1965 | Bentov | 128/785 |
| 4,141,365 | 2/1979 | Fischell et al. | 128/642 |
| 4,219,027 | 8/1980 | Lund | 128/642 |
| 4,281,660 | 8/1981 | Fujiwara | 128/785 |
| 4,285,347 | 8/1981 | Hess | 128/785 |
| 4,323,081 | 4/1982 | Wiebusch | 128/785 |
| 4,345,606 | 8/1982 | Littleford | 128/419 P |

OTHER PUBLICATIONS

Caldwell et al., "Percutaneous Wire Electrode . . . ", 9-9-74.

Primary Examiner—Lee S. Cohen
Assistant Examiner—Steven Falk
Attorney, Agent, or Firm—Lockwood, Alex, Fitzgibbon & Cummings

[57] ABSTRACT

A method for the introduction and fixation of a neural stimulator lead in the epidural space of a patient's spinal cord includes the percutaneous placement of a pair of spaced Tuohy needles such that their open tips are in the patient's epidural space and the open tips of the needles are spaced from and face each other. A surrogate lead is inserted through the caudad needle and its leading distal end is moved through the epidural space until it is adjacent the opening in the cephalad needle. A snare is inserted through the cephalad needle to snare the distal end of the surrogate lead and the surrogate lead is drawn through the cephalad needle with the snare. The conductive neural stimulator lead is coupled to the trailing end of the surrogate lead and the surrogate lead is withdrawn through the caudad needle drawing the neural stimulator lead through the epidural space until its electrode is positioned at the location on the dura to be stimulated. Upon such positioning of the neural stimulator electrode, the Tuohy needles are removed and both ends of the neural stimulator lead are fixed in the patient's body.

12 Claims, 12 Drawing Figures

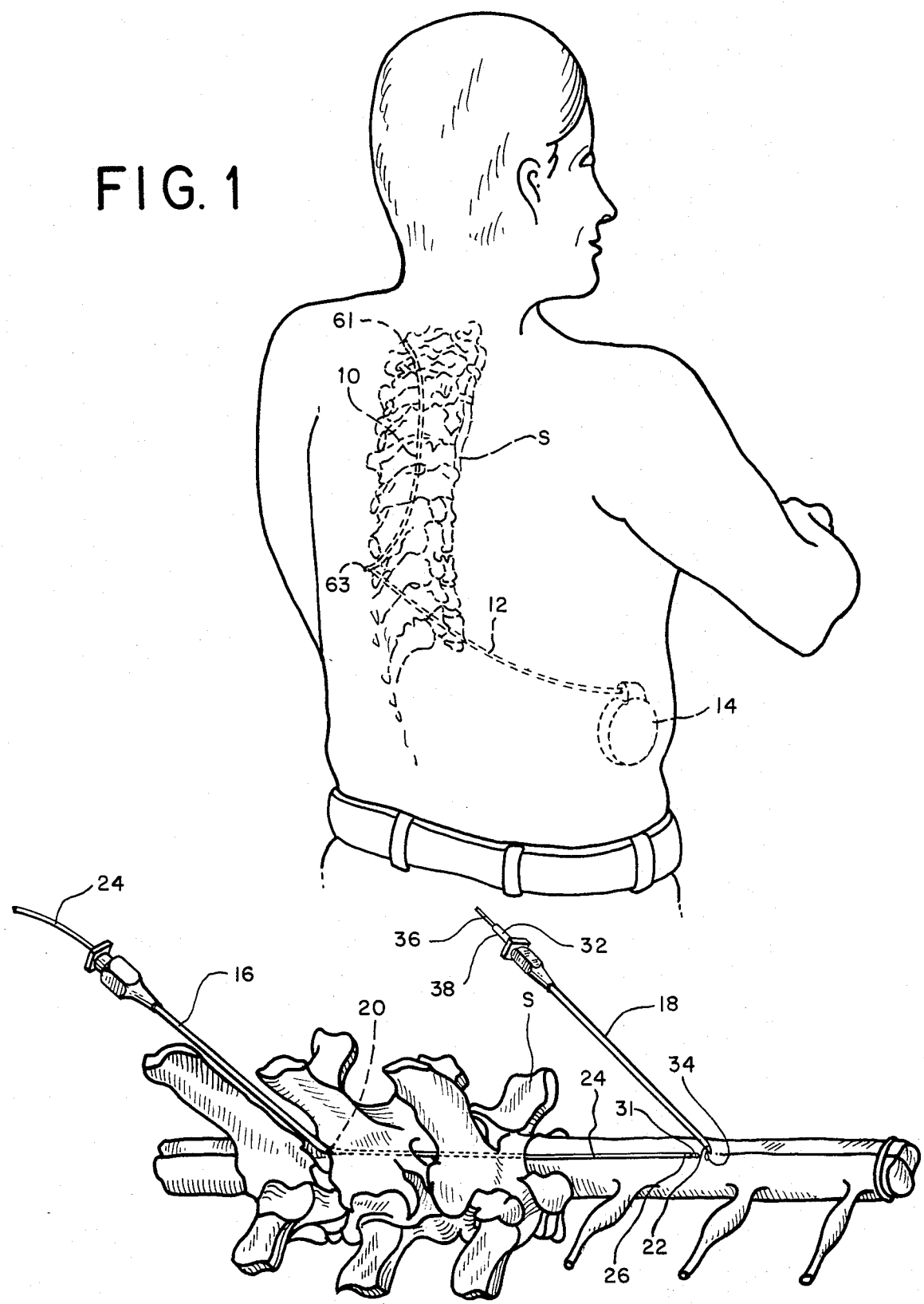

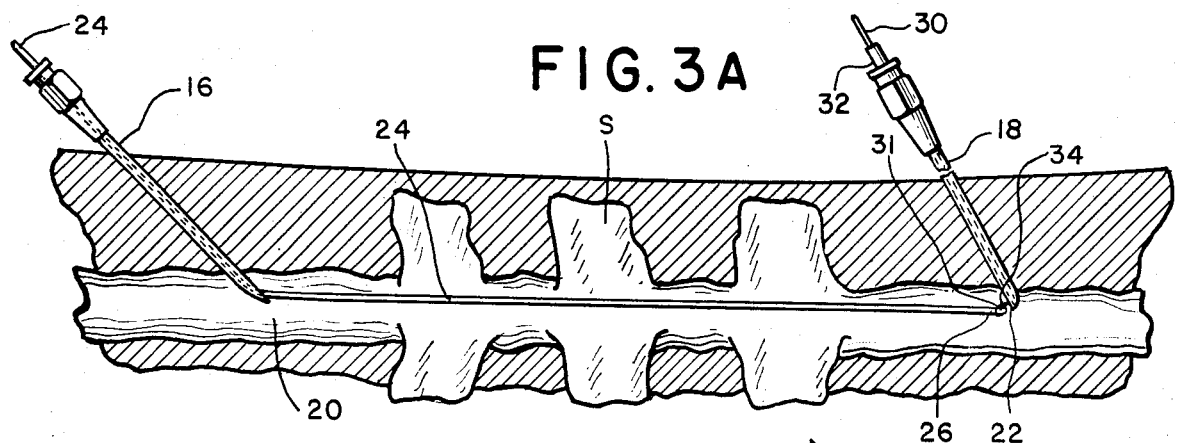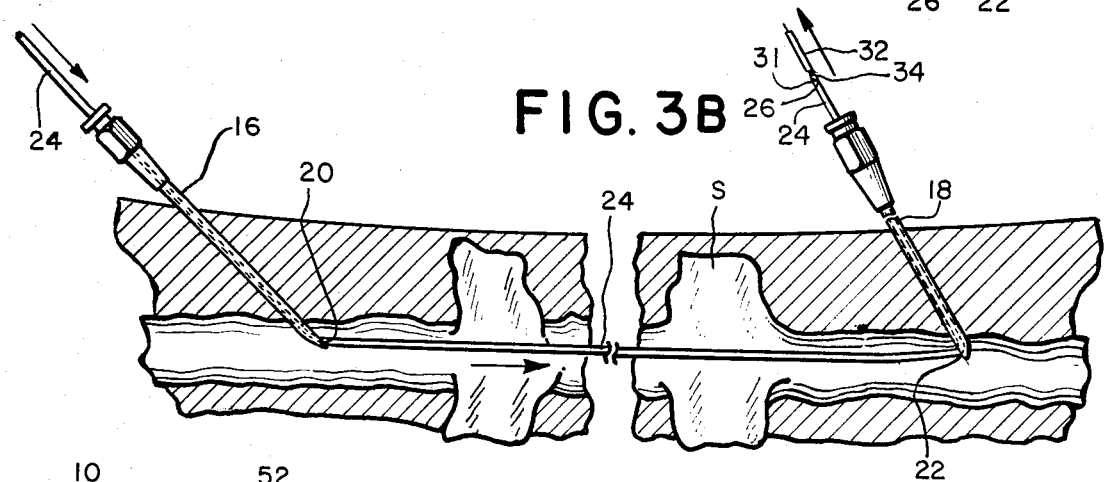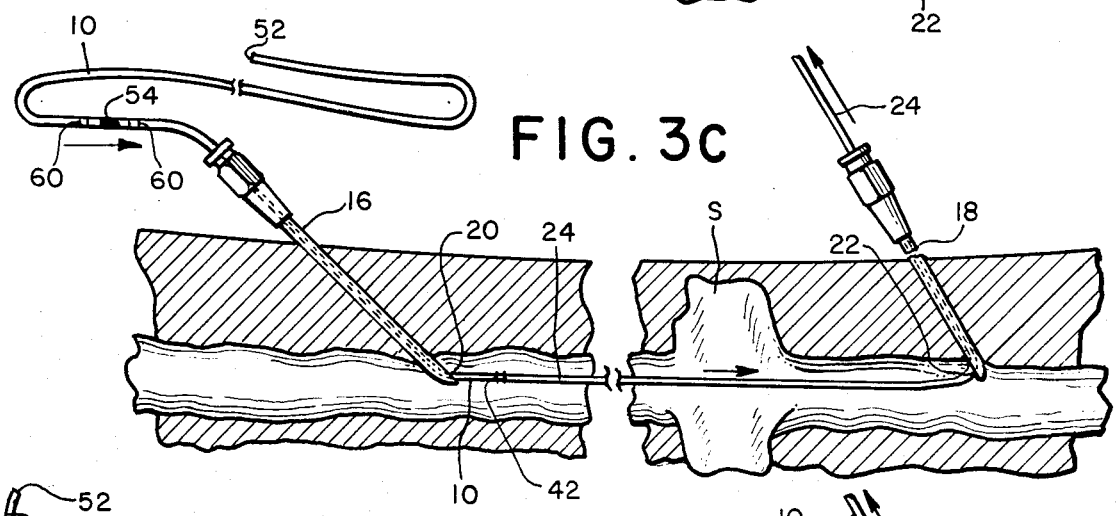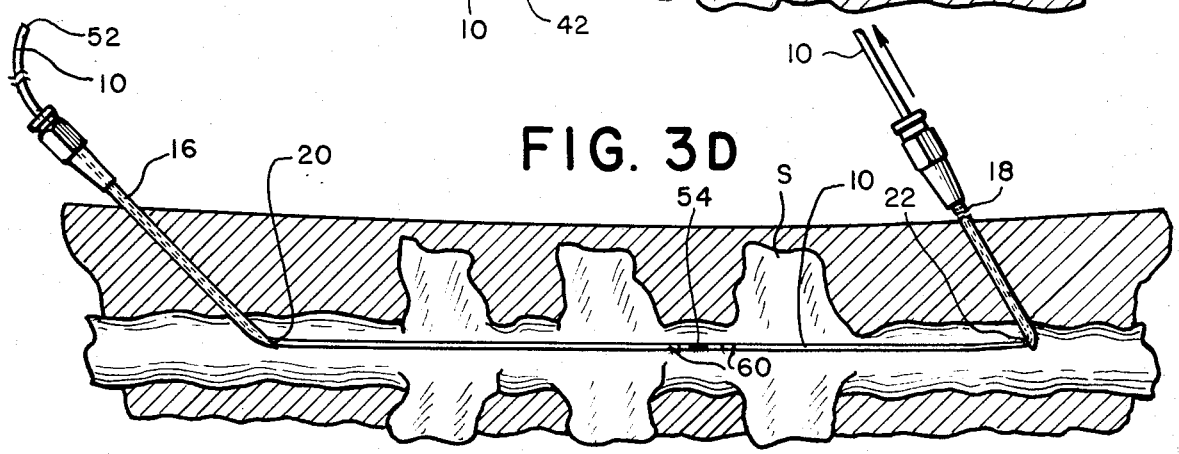

METHOD FOR LEAD INTRODUCTION AND FIXATION

BACKGROUND AND SUMMARY OF THE INVENTION

The present invention relates to a method for lead introduction and fixation and, more particularly, to a method for the introduction and fixation of a neural stimulator lead in the epidural space of the spinal cord of a patient.

Neural stimulator electrodes and leads have been employed in the past which have been implanted in the epidural space of the spinal cord of a patient for stimulating selected locations along the spinal cord for such purposes as the relief of pain. One method of introduction and implantation is disclosed in U.S. Pat. No. 4,285,347. In that patent a neural stimulator lead is disclosed in which the leading distal end of the lead is axially moved along the epidural space in the spinal cord by passing the end through a Tuohy needle and pushing the end of the lead to the location on the dura where it is to stimulate the spinal cord. The lead disclosed in that patent has a configuration at its distal end and adjacent the stimulating electrode which may be deformed during installation of the lead by a stylet which passes through the lead to minimize the pain and trauma to the patient. Once the lead has been positioned as desired, the stylet is removed to cause the distal end of the lead to expand to minimize subsequent axial or lateral movement of the lead once it has been placed.

The method of introduction and fixation incorporating the principles of the present invention realizes several advantages over the prior methods of placement and fixation of neural stimulator leads. A method incorporating the principles of the present invention greatly facilitates the positioning of the lead electrodes with a minimum of effort and a minimum of trauma to the patient and essentially precludes the need for repositioning of the lead once it has been positioned. A method incorporating the principles of the present invention enables fixation of the lead at two points, thus minimizing the possibility of axial or lateral movement of the lead once it has been installed. A method incorporating the principles of the present invention may also eliminate the need for the use of a stylet during installation, thereby minimizing pain and trauma to the patient which might be associated with the installation and fixation procedure. A method incorporating the principles of the present invention enables precise control of the lead during installation and fixation by providing for manipulation simultaneously of both ends of the lead.

In one principal aspect of the present invention, a method of introduction of a percutaneous conductive lead in the body of a patient for implantation of the lead therein includes inserting first and second hollow needles through the skin of the patient to a subcutaneous depth at which the lead is to be fixed. The tips of the needles are spaced from each other on opposite sides of the location which is to be stimulated by the lead and the tips of the needles are positioned to face each other. A lead is inserted through the first hollow needle and the lead is passed through the patient's body until its leading distal end is adjacent the tip of the second needle. A snare is inserted through the second needle and the leading distal end of the last mentioned lead is snared and pulled through the second hollow needle so that the last mentioned lead extends from the patient's body through both of the hollow needles.

In another principal aspect of the present invention, the last mentioned lead is a surrogate lead. After the surrogate lead has been snared and pulled through the second needle, one of the ends of the surrogate lead is attached to the conductive lead and the conductive lead is pulled completely through one of the needles at least to the tip of the other needle, and the attached end of the conductive lead is further pulled such that both ends of the conductive lead extend from the patient's body.

In still another principal aspect of the present invention, the conductive lead is a neural stimulator lead for stimulating the spinal cord of a patient and the needles and the conductive lead are inserted into the epidural space of the patient's spinal canal.

These and other objects, features and advantages of the present invention will be clearly understood through a consideration of the following detailed description.

BRIEF DESCRIPTION OF THE DRAWINGS

In the course of this description, reference will frequently be made to the attached drawings in which:

FIG. 1 is an overall perspective view of a patient in which a neural stimulator has been installed and fixed in accordance with the principles of the present invention;

FIG. 2 is a broken view of a portion of the vertebrae and spinal cord of the patient in which the surrogate lead of the present invention has been positioned in readiness to be snared;

FIG. 3A is a broken, partially cross-sectioned view of the patient's spinal cord and in which the surrogate lead has been snared;

FIG. 3B is a view similar to FIG. 3A, but in which the snared surrogate lead has been pulled through both of the Tuohy needles;

FIG. 3C is a view similar to FIG. 3B, but in which the neural stimulator lead has been coupled to the trailing end of the surrogate lead and has been pulled through one of the needles;

FIG. 3D is a view similar to FIG. 3C, but in which the neural stimulator lead has been positioned at its desired epidural location and its leading distal end has been drawn through the other needle;

DESCRIPTION OF THE PREFERRED EMBODIMENT

Figure 3E:
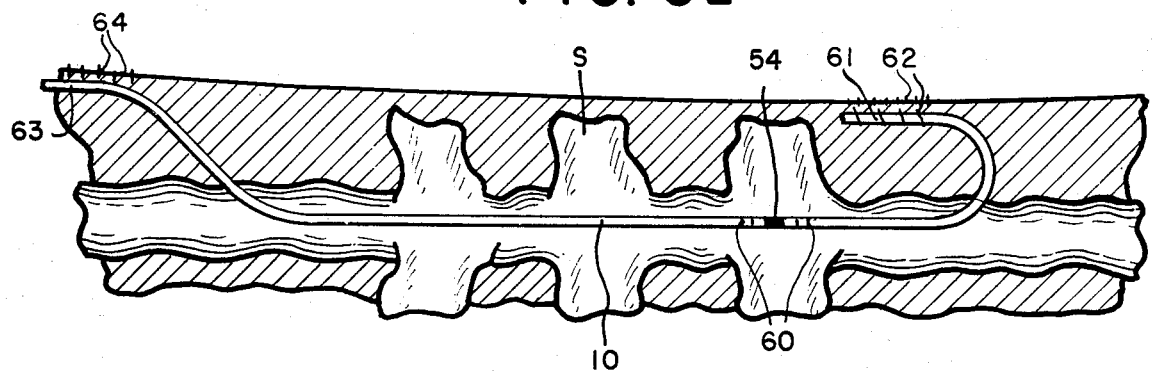
FIG. 3E is a view similar to FIG. 3D, but in which the needles have been removed and the neural stimulator lead has been fixed.

The present invention is directed to a method of installing and fixing a neural stimulator lead 10 in the epidural space of the spinal cord of a patient. As shown in FIG. 1, the lead 10 is positioned in the epidural space in the patient's spinal column S and extends axially in that space. The lower distal end, or caudad end, of the lead is electrically connected, preferably subcutaneously, to a connector conductor 12. The connector conductor 12 also preferably extends subcutaneously and, in turn, is connected to a preferably subcutaneously implanted stimulator which generates electrical pulses or signals, as is known in the art, for stimulating one or more predetermined locations along the patient's spinal cord.

Installation of the neural stimulator lead 10 in accordance with the principles of the present invention begins by percutaneously positioning a pair of spaced Tuohy needles 16 and 18 through the skin of the patient as shown in FIG. 2. The construction of the Tuohy needles will not be described in detail as they are conventional and have been previously employed in a number of medical procedures, including the installation of neural stimulator leads. Each of the needles is hollow and may be of conventional cross-section shapes. One of the needles 16, the caudad or lower needle, is positioned as shown in FIG. 2 so that its lower open end 20 is located in the epidural space and pointing cephalad. The other needle 18, or cephalad needle, is also positioned so that its opening 22 is positioned in the epidural space and is then rotated as necessary so that its opening 22 faces caudad and the opening 20 of needle 16.

At this point a precursor surrogate lead 24 is inserted through the upper end of the caudad needle 16, down through the needle 16, and the distal end 26 of the surrogate lead is pushed axially along the epidural space until it is adjacent the opening 22 in the cephalad needle 18.

The surrogate lead 24 is preferably formed of a helically wound wire 28 which is biologically compatible, such as stainless steel. The helical winding has the advantage of lying straight, thereby facilitating threading of the lead through the epidural space with a minimum of injury and trauma to the patient. The wire 28 is preferably encapsulated in a suitable biologically compatible coating 30, such as polyurethane, Teflon or Silastic, to further cushion the surrogate lead and minimize the possibility of injury or trauma to the patient. The distal end 26 of the surrogate lead is preferably grooved to facilitate snaring, as will next be discussed. The groove may either take the form of a bulbous shape 31, as best shown in FIG. 4, or, in the alternative, may be notched.

Once the distal end 26 of the surrogate lead 24 has been positioned adjacent the opening 22 in the cephalad needle 18, a snare 32, having a loop 34 at its leading end, is inserted through the cephalad needle 18 until the loop 34 just extends beyond the opening 22 of the needle. Entry of the loop into the epidural space will cause it to pitch downward slightly as shown in FIG. 2 to maximize exposure to the loop for threading of the distal end 26 of the surrogate lead 24 and its bulbous tip 31 through the loop.

Figure 4:
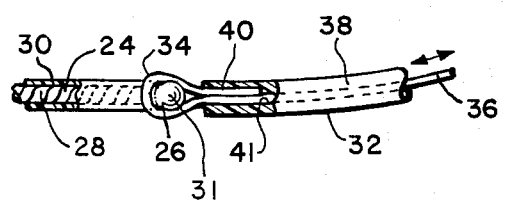
FIG. 4 is an enlarged, partially broken cross-sectioned plan view showing the snare snaring the leading distal end of the surrogate lead similar to the step shown in FIG. 3A.

The snare 32 preferably comprises a single stainless steel wire 36 as shown in FIGS. 2 and 4 which preferably passes through a hollow encasing tubing 38. The wire 36 is preferably a straight wire as shown in FIG. 4, but may be helical, if desired. The tubing 38, likewise, is preferably formed of a suitable biologically compatible material, such as Silastic, Teflon or polyurethane. Although the use of tubing 38 is shown, the tubing might be eliminated where the leading end of the surrogate lead 24 is notched or otherwise formed to cooperate with the snare loop 34. Where the tubing 38 is employed the loop 34 is formed at one end of the wire by looping the wire 36 back upon itself as shown in FIG. 4 and the distal end 40 of the wire is preferably fixed at the end of the tubing 38, such as by embedding the wire end 40 in the tubing as shown in FIG. 4. If the tubing 38 is eliminated, the wire 36 is bent back upon itself to form the loop.

The lumen 41 through the tubing 38 has a diameter which is preferably just large enough to allow axial movement of the wire 36 therein so as to allow selective enlargement or contraction of the size of the loop 34 to enable threading of the distal end 26 of the surrogate lead 24, and also snaring of that lead once it has been threaded through the loop. By embedding the distal end 40 of the wire 36 at the end of the tubing 38, only a single length of the wire need pass through the tubing, thus minimizing the diameter of the snare tubing 38. It will, however, be understood that the wire need not be embedded as shown in FIG. 4 and both legs of the loop wire may pass down the tubing, if tubing diameter is not a concern or the tubing may be eliminated altogether as previously discussed. The end of the wire 36 opposite the loop preferably extends beyond the exterior end of the tubing 38, as shown in FIGS. 2 and 3A, to allow manipulation of the wire to alter the size of the loop.

Once the distal end 26 of the surrogate lead 24 and its bulbous tip 31 have been snared by the loop 34 as shown in FIG. 3A, the snare 32 is withdrawn from the cephalad Tuohy needle 18 as shown in FIG. 3B. When the snare is withdrawn, the surrogate lead 24 now extends through both of the needles. Alternatively, if for some reason the snared surrogate lead end fails to pass through the opening of the cephalad needle 18, the needle may be withdrawn together with the snared leading end 26 of the surrogate lead.

Figure 5:
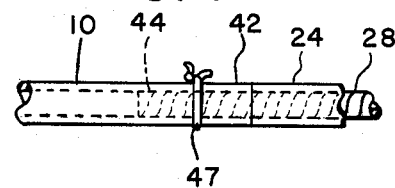
FIG. 5 is an enlarged, partially broken plan view of a suitable manner of coupling the trailing end of the surrogate lead to the leading distal end of the neural stimulator lead similar to the step shown in FIG. 3C.
Figure 6:
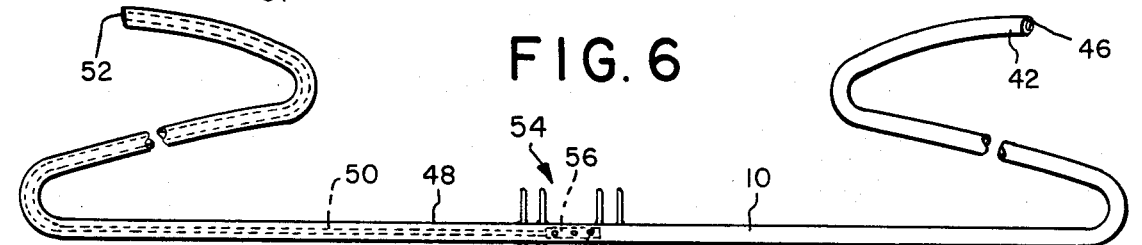
FIG. 6 is an overall elevation view of a preferred embodiment of neural stimulator lead.

Either at this point in time or before the snare is withdrawn from needle 18, the leading distal end 42 of the neural stimulator lead 10 may be coupled as shown in FIGS. 3C and 5 to the trailing end 44 of the surrogate lead 24. Such coupling may be accomplished by inserting the trailing end 44 of the surrogate lead into the opening 46 of the lead 10 as shown in FIG. 6. Opening 46 may be defined by the lumen through the neural stimulator lead which would otherwise contain the lead conductor. Such coupling occurs at a time when the trailing end 44 of the surrogate lead 24 still extends outside of the caudad needle 16 as shown in FIG. 3B. The coupling may be secured by tying off with a suture 47, as shown in FIG. 5, to prevent separation of the surrogate and neural stimulator leads as they are being drawn through the epidural space.

Figure 7:
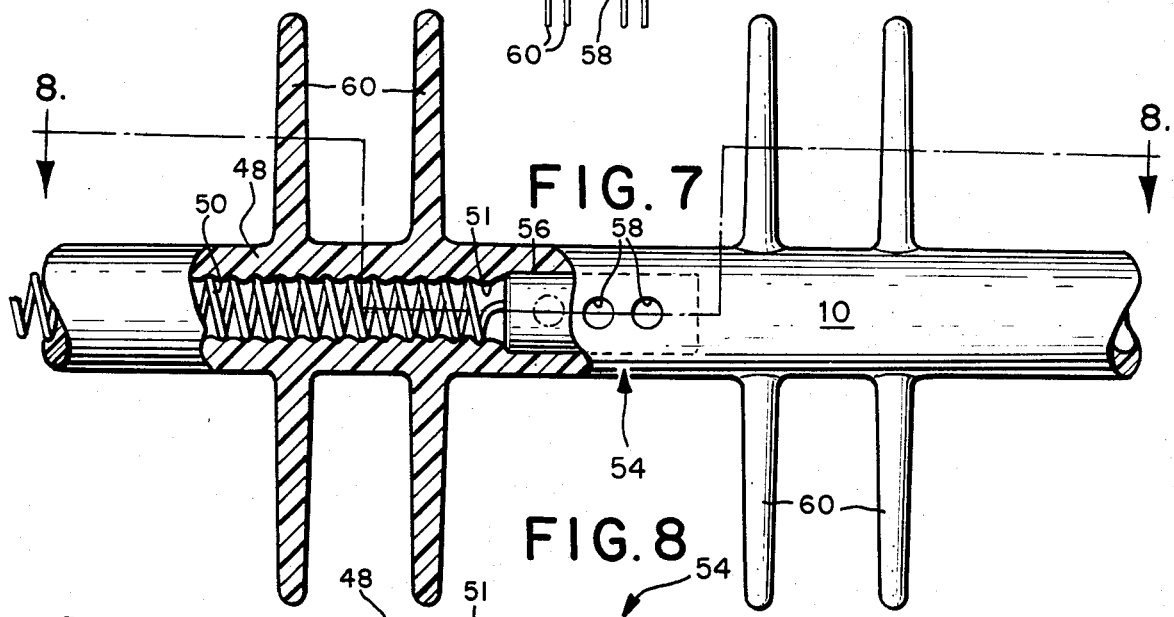
FIG. 7 is a partially broken elevation view of the electrical contact region of the lead shown in FIG. 6.
Figure 8:
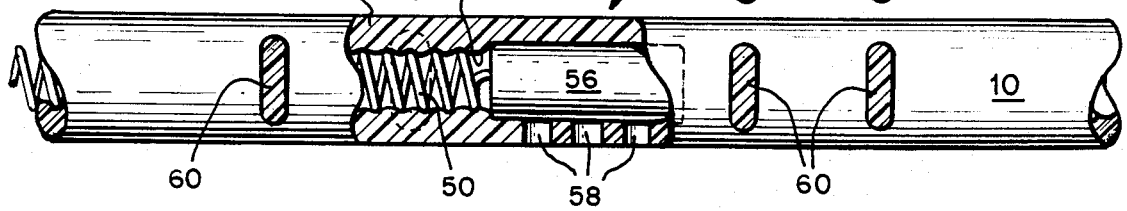
FIG. 8 is a partially broken plan view of the electrical contact region of the lead as viewed substantially along line 8—8 of FIG. 7.

As shown particularly in FIGS. 6-8, the neural stimulator lead 10 preferably comprises an elongate flexible tube 48 formed of a biologically compatible material, such as Silastic, Teflon or polyurethane, and the tube 48 is preferably hollow over its length. One or more electrical conductors, such as the helical conductor 50 as shown in FIGS. 7 and 8, extends through the hollow lumen 51 through one side of the lead 10. Following installation, the end 52 of the conductor 50 is cut to its desired length and terminated with a suitable terminal (not shown) for coupling the lead 10 to the conductor 12. The other end of the conductor 50 terminates in an electrical contact region, generally 54 as shown in FIGS. 6-8, intermediate the length of the lead. This contact region includes an electrode 56 which may be formed of platinum or other biologically compatible metal. The electrode 56 is embedded in the tubing 48, but is exposed to the exterior of the tubing, such as by openings 58, to allow the body fluids to contact the electrode.

The neural stimulator lead 10 may also include one or more flexible projections adjacent the electrical contact region 54 to stabilize the electrode against axial or lateral displacement and fix the electrode in its desired implanted position at the location on the dura. By way of example, such projections may take the form of laterally extending flexible wings 60, as best shown in FIGS. 6-8. The wings 60 are very flexible to allow drawing of the lead through the epidural space during installation of the lead. The length of the wings 60 may vary, but is preferably on the order of about twice the diameter of the tube 48 of the lead 10. Although the wings 60 are shown as extending substantially perpendicularly from the lead, it will be understood that they might extend at an acute angle thereto.

Returning to a description of the installation of the lead, once the trailing end 44 of the surrogate lead 24 has been coupled to the neural stimulator lead 10, as shown in FIG. 5, the surrogate lead is withdrawn from the cephalad needle 18, as shown in FIG. 3C, and the neural stimulator lead 10 is drawn into the epidural space through the caudad needle 16.

Alternatively, the neural stimulator lead 10 may be coupled to the leading end of the surrogate lead 24 which extends from the cephalad needle 18. In this case, the surrogate lead 24 is pulled back through the cephalad and caudad needles 18 and 16, respectively, to withdraw the surrogate lead and to draw the neural stimulator lead from cephalad to caudad in the reverse direction. Whichever drawing procedure is used, drawing is continued until the electrical contact region 54 and its electrode 56 are positioned at the desired location in the epidural space. Control of the positioning of the lead 10 is greatly facilitated due to the fact that both ends of the lead 10 may be readily manipulated because both ends extend from the respective Tuohy needles 16 and 18.

Once the electrode 56 is positioned in its desired location, the Tuohy needles 16 and 18 are both removed, if they had not been removed earlier. The leading distal end of the stimulator lead 10 is cut to a suitable length to allow for some slight looping to relieve strain on the lead and to sever the surrogate lead 24 and its trailing end 44, as shown in FIG. 5, from the neural stimulator lead 10. The tubing opening 46 at the cut is preferably sealed by a suitable polymer or the like, either as made or at the time of cutting, to prevent entry of body fluids into the lead end of the lead 10. This cephalad end 61 of the lead 10 is then positioned subcutaneously and the lead and the incision is sutured by sutures 62 as shown in FIG. 3E, to fix the lead. The trailing caudad end 63 of the lead 10 is coupled, preferably subcutaneously, to conductor 12 and to the stimulator 14, both of which are also preferably subcutaneously located. The incision at the trailing caudad end 63 of the lead is also sutured, as by sutures 64 shown in FIG. 3E, to fix the caudad end 63 of the lead 10.

From the above description it will be seen that the neural stimulator lead 10 and its electrical contact region 54 may be readily and accurately initially positioned by manipulation of both ends of the lead 10. Moreover, it will be seen that the method incorporating the principles of the present invention may eliminate the need altogether for the use of a stylet during installation and the potential disadvantages associated with such use and the need to reposition the lead once it is installed and fixed is substantially eliminated because the stimulator lead 10 may be secured at both ends once the lead has been positioned.

The above described method of installation and fixation of the lead is of course greatly facilitated by utilizing X-ray fluoroscopy, ultrasonic imaging and other known techniques during the installation and fixation. Accordingly, the various elements, such as the stimulator lead 10, the needles 16 and 18, the surrogate lead 24 and the snare 32 are all preferably formed of radiopaque material.

Although a single electrode 56 only is shown in the neural stimulator lead 10, the neural stimulator lead may include more than one electrode as desired. Moreover, even though the above described method of installation and fixation has been described in terms of feeding the various components through the caudad needle 16 and removing the components through the cephalad needle 18, the direction of insertion and drawing may be reversed as desired.

It will also be understood that the embodiment of the present invention which has been described is merely illustrative of one of the applications of the principles of the present invention. Numerous modifications may be made by those skilled in the art without departing from the true spirit and scope of the invention.

What is claimed is:

1. A method of introduction of a percutaneous conductive lead into the body of a patient for implantation of the lead therein, including:
    inserting first and second hollow needles through the skin of the patient to a subcutaneous depth at which the lead is to be fixed; the tips of said needles being spaced from each other on opposite sides of a location to be stimulated by said lead;
    positioning the tips of said needle; to face each other;
    inserting a surrogate lead through said first hollow needle;
    passing said surrogate lead through the patient's body until its leading distal end is adjacent the tip of said second needle;
    inserting a snare through said second needle and snaring the leading distal end of said surrogate lead;
    pulling said snare and snared leading distal end of said surrogate lead through said second hollow needle so that said surrogate lead extends from the patient's body through both of said hollow needles;
    attaching one end of said surrogate lead to an end of the conductive lead; and pulling said surrogate lead to pull said conductive lead into the body of the patient.

2. The method of claim 1, wherein said surrogate lead is further pulled such that both ends of the conductive lead extend from the patient's body.

3. The method of claim 2, wherein said first and second needles are Tuohy needles.

4. The method of claim 1, wherein said first and second needles are Tuohy needles.

5. The method of claim 2, wherein said conductive lead includes a contact region thereon for electrically stimulating the patient and said contact region is positioned at the location to be stimulated while both ends of said conductive lead extend from the patient's body, said needles are removed from the patient's body, and said conductive lead is secured to the patient's body adjacent the location from which both of the needles have been removed and after said contact region has been positioned at the location to be stimulated.

6. The method of claim 1, wherein said conductive lead is a neural stimulator lead for stimulating the spinal cord of the patient, and said needles and said conductive lead are inserted into the epidural space of the patient's spinal canal.

7. The method of claim 2, wherein said conductive lead is a neural stimulator lead for stimulating the spinal cord of the patient, and said needles and said conductive lead are inserted into the epidural space of the patient's spinal canal.

8. The method of claim 5, wherein said conductive lead is a neural stimulator lead for stimulating the spinal cord of the patient, and said needles and said conductive lead are inserted into the epidural space of the patient's spinal canal.

9. The method of claim 8, wherein said first and second needles are Tuohy needles.

10. The method of claim 2, wherein said conductive lead is pulled through both of said needles and said needles are thereafter removed from the patient's body.

11. The method of claim 2, wherein said snare snares grooved means to facilitate snaring at the leading distal end of said surrogate lead.

12. A method of fixing a conductive neural stimulator lead in the body of a patient including:
positioning the conductive lead in the epidural space of the patient's spinal canal so that it exits the body at two spaced locations through the skin of the patient, and
securing the lead to the patient's body adjacent both of said locations.

* * * * *